United States Patent [19]
Whalen

[11] Patent Number: 5,634,892
[45] Date of Patent: Jun. 3, 1997

[54] EXTRACORPOREAL MEMBRANE OXYGENATOR

[76] Inventor: Robert L. Whalen, 11 Miller St., Somerville, Mass. 02143

[21] Appl. No.: 393,279

[22] Filed: Feb. 23, 1995

[51] Int. Cl.$^6$ .................................................. A61M 37/00
[52] U.S. Cl. ........................ 604/4; 422/46; 261/DIG. 28
[58] Field of Search ................ 422/46, 48; 261/DIG. 28; 604/4

[56] References Cited

U.S. PATENT DOCUMENTS

| | | | |
|---|---|---|---|
| 3,841,837 | 10/1974 | Kitrilakis | 261/DIG. 28 |
| 3,890,969 | 6/1975 | Fischel | 422/46 |
| 4,328,102 | 5/1982 | Bellhouse | 261/DIG. 28 |
| 4,883,455 | 11/1989 | Leonard | 422/46 |
| 5,043,140 | 8/1991 | Combs | 422/46 |
| 5,188,801 | 2/1993 | Fini | 261/DIG. 28 |
| 5,192,499 | 3/1993 | Sakai | 261/DIG. 28 |
| 5,236,665 | 8/1993 | Mathewson | 261/DIG. 28 |
| 5,270,005 | 12/1993 | Raible | 261/DIG. 28 |
| 5,277,176 | 1/1994 | Habashi | 261/DIG. 28 |

*Primary Examiner*—Michael J. Milano

[57] ABSTRACT

An extracorporeal membrane pump/oxygenator for extracorporeal cardiopulmonary support, which employs a two stage pump system in combination with a membrane oxygenator enclosed in a housing. Where the first pump, in the current embodiment, is an axial flow pump whose primary function is to create secondary flows in the oxygenator at low pressures, and the second pump, in the current embodiment, is a servo-controlled centrifugal pump whose function is to return oxygenated blood back to the patient. It provides the energy needed to overcome the resistance of the return line, and to maintain forward flow at either aortic or venous pressures, thus permitting the use of either veno-arterial or veno-venous bypass. The oxygenator portion of the device consists of two readily made cylindrical membranes suspended to form a tubular flow channel. Blood passing through the oxygenator follows a complicated spiral path such that its effective contact time with the gas exchange membranes is prolonged.

5 Claims, 3 Drawing Sheets

EXTRACORPOREAL MEMBRANE OXYGENATOR

BACKGROUND—DESCRIPTION OF PRIOR ART

Respiratory failure requiring pulmonary support affects in excess of 300,000 people in the United States per year. Approximately one-half of these patients suffer from adult respiratory distress syndrome (ARDS). Adult respiratory distress syndrome is an acute inflammatory lung disease with a mortality rate of 50%. This disease is characterized by increased capillary permeability resulting from the development of interstitial edema and alveolar flooding.

For the vast majority of patients with ARDS, there is no specific treatment, or supportive therapy. Supportive therapy for ARDS focuses on mechanical ventilation. Mechanical ventilation, by creating a positive pressure gradient, results in the inflation of the lungs. This is a reversal of the normal lung which functions by utilizing negative pressures to ventilate the lung.

Current ventilatory support may be damaging to the lung. Pulmonary "Volutrauma" secondary to high ventilator tidal volumes and airway pressures may cause a capillary leak syndrome pathologically indistinguishable from ARDS. Thus, alternative life support modalities such as extracorporeal membrane oxygenation (ECMO) may be a therapeutic option for acute respiratory failure in both infants and adults.

Oxygenators developed to date are broadly classified into bubble type and oxygenators and membrane type oxygenators. The membrane type oxygenators fall under the laminate type, the coil type, and the hollow fiber type. Membrane type oxygenators excel over the bubble type oxygenators since the membrane type oxygenators cause minimal blood damage, such as hemolysis, protein denaturation, and blood coagulation as compared with the bubble type oxygenators.

With the true efficacy of membrane oxygenators finally being realized, increasing success for the past decade has been realized in acute respiratory failure of the term gestation newborn. Encouraging results with extra corporeal membrane oxygenation (ECMO), has also been reported in the support of pediatric patients with life threatening pulmonary, or pulmonary vascular disease.

Despite the over 5,000 use of ECMO in the newborn by 1992, hardware innovation in this area has lagged far behind clinical advances. In fact, the ECMO circuit used today is remarkably similar to that reported over 20 years ago by Kolobow U.S. Pat. No. 3,969,240. As a result, progress in dealing with some of the more significant complications associated with ECMO support has been slow. These complications chiefly result from ECMO induced thrombocytopenia, the need for heparinization, and carotid artery ligation. The most commonly seen complications include intracranial bleeding, seizures, and post-ECMO functional deficits.

A typical pediatric ECMO circuit is composed of numerous components which include a venous reservoir, a roller (or impeller) pump, a membrane oxygenator, a heat exchanger, polyvinylchloride connecting tubing, and connectors. Blood is passively drained by gravity from the venous circulation using a siphon height of 100 cm or more into a collapsible bladder that acts as a compliant reservoir. The bladder has a proximity switch attached to its top surface that acts to regulate the roller pump by turning it off when the bladder deflates.

This mechanism limits the maximum suction applied to the patient to the hydrostatic pressure created by the siphon. Blood then passes through an occlusive roller pump and is forced at flow rates ranging from 120 to 170 ml/min/kg through a membrane oxygenator, such as a Kolobow U.S. Pat. No. 3,969,240. Oxygenated and $CO_2$ cleared blood is then returned via a heat exchanger at body temperature back to the patient's circulation.

There are some obvious deficiencies associated with this type of system. These include: (1) a large area of contact between blood and potentially thrombogenic surfaces requiring substantial I.V. doses of heparin; (2) a relatively complex physical set-up which requires comparatively long runs of tubing subject to accidental kinking or catastrophic disconnection; and (3) a cumbersome and awkward method of regulating bypass flow rate, namely raising or lowering the whole apparatus to change the siphon pressure.

U.S. Pat. No 3,856,475 to Marx discloses a device for transferring oxygen into blood. Oxygen is dissolved into a fluorocarbon transfer medium. Oxygen depleted blood passes through a multiplicity of small diameter, blood gas pervious silicon membrane transporting tubes. The oxygen is transferred through the walls of the tube to the blood using direct gas infusion to the gas exchange medium, resulting in a non-homogeneous gas transfer medium secondary to bubble formation. Blood is propelled through the apparatus by compressing the gas exchange tubes.

U.S. Pat. No. 5,294,401 discloses a membrane type oxygenator for effecting exchange of gases with a porous gas exchange membrane possessing minute through pores forming a path for gas, which membrane type oxygenator is characterized by the fact that minute particles are retained in the minute pores of the porous gas exchange membrane to permit a decrease in the cross sectional area of the path for gas and as blood anticoagulant is retained in the minute particles or between the minute particles.

U.S. Pat. No. 5,277,176 discloses an Extracorporeal lung assistance apparatus and process which has an oxygen containing gas chamber positioned in such a relationship to a gas exchange chamber that transfer of oxygen to blood and the withdrawal of carbon dioxide from the blood. The above cited prior art, however, does not apply to neonate extracorporeal membrane oxygenators.

ECMO in neonates is also complicated by the low circulating blood volume of the patients and by the difficulty of obtaining vascular access. The total blood volume of a neonate is generally appreciably less than the priming volume of the typical ECMO circuit. A volume of donor blood equivalent to several total exchange transfusions is thus required simply to prime the circuit.

Therefore, a compact, simple to use pump/oxygenator system with reduced blood contacting surface area and automatic control would be an improvement in the treatment of acute respiratory insufficiency in both adult and neonatal patients. The present invention employs a two stage pump system in combination with a membrane oxygenator. The first pump is an axial flow pump whose primary function is to create secondary flows in the oxygenator at low pressure. Another function of the first pump is to provide controlled suction such that the hydrostatic suction, and venous reservoir required with conventional systems can be eliminated.

Since the laminar flow fluid boundary layer in membrane oxygenators is known to contribute the majority of diffusional resistance to gas transfer, the effect of induced secondary flows is to improve the membrane gas transfer efficiency, in this way, the membrane surface area required for adequate gas exchange may be reduced and the contact of blood with synthetic surfaces minimized.

The oxygenator portion of the invention consists of two readily made cylindrical membranes suspended in a housing to form a tubular flow channel. Blood passing through the oxygenator follows a complicated spiral path such that its effective contact time with the gas exchange membranes is prolonged.

The comparatively high fluid shear rates provided by the axial flow pump, in combination with smooth inflow and outflow transitions in the oxygenator, minimize the potential for thrombus formation. The second pump in the system is a servo-controlled centrifugal pump whose function is to return oxygenated blood back to the patient. It provides the energy needed to overcome the resistance of the return line and to maintain forward flow at either aortic or venous pressures, thus permitting the use of either veno-arterial or veno-venous bypass.

The control system of the new device employs fuzzy logic. The control system will automatically adjust the rotational rate of the centrifugal pump to maintain a low positive pressure in the oxygenator as the flow rate of the system is changed either in response to operator input or changing venous return flow, or to changes in the afterload pressure.

A compact and simple to use pump/oxygenator system with reduced blood contacting surface area and automatic control, combined with enhanced membrane transfer efficiency is a significant improvement in the treatment of acute respiratory insufficiency in adult and neonatal patients.

SUMMARY OF THE INVENTION

With the above in view, it is therefore the general object of the present invention to provide a pump/oxygenator for extracorporeal cardiopulmonary support, wherein the invention employs a two stage pump system in combination with a membrane oxygenator, wherein the first stage pump provides initial secondary flow providing a complicated spiral path for the blood thereby creating greater membrane efficiency by decreasing the diffusional area required for blood oxygenation, wherein the second stage pump is a centrifugal pump for returning the oxgenated blood to the patient while maintaining low positive pressures by means of a servo controlled mechanism.

It is another object of the invention to create an oxygenator which utilizes secondary flows by means of an axial flow pump, whereby the secondary flows increase membrane transfer efficiency by confining flow through the oxygenator to a tubular cross sectional space after it passes said axial flow pump, thereby breaking up the boundary layer on said membrane thereby promoting gas exchange.

It is another object of the invention to lessen the potential for thrombus formation by providing an oxygenator that utilizes secondary flow, and said secondary flow is so high that shear rates inside the oxygenator are sufficient enough to prevent the formation of thrombi.

It is yet another object of the present invention to return the oxygenated blood back to the patient by means of a centrifugal pump.

It is another object of the invention to provide a centrifugal outflow pump which is servo controlled to maintain oxygenator pressure in a fixed range regardless of afterload pressure by means of a servo controller mechanism.

It is yet another object of the present invention to provide an automatic control system that functions by adjusting the rotational rate of the outflow pump so that a low positive pressure is maintained in the oxygenator at all times independent of flow rate or afterload pressure.

It is still yet another object of the invention to provide a membrane oxygenator comprised of concentrically mounted ultra thin membranes comprised of a material such as polyflourinated cellulose or polyalkylsulfones, contained in a clear plastic housing comprised of a material such as polycarbonate.

It is yet another object of the invention to provide a membrane oxygenator comprised of concentrically mounted ultra thin membranes comprised of a material such as polyflourinated cellulose or polyalkylsulfones, contained in a clear plastic housing comprised of a material such as polycarbonate, with said membranes being mounted on an elastomeric ring, where said elastomeric ring is chemically bonded to the exterior of the membranes and mechanically clamped to the housing.

It is still another object of the invention provide a membrane oxygenator comprised of concentrically mounted ultra thin membranes comprised of a material such as polyflourinated cellulose or polyalkylsulfones, contained in a clear plastic housing comprised of a material such as polycarbonate, with said membranes being mounted on an elastomeric ring,wherein both membranes have included as a support structure on the inside backing of each membrane a longitudinal wire support providing longitudinal corrugations in the tubular membranes.

It is another object of the invention to provide a pump oxygenator containing both an inflow and outflow pump where said outflow pump contains an automatic control system which functions by adjusting the rotational rate of said outflow pump, providing low positive pressures in said oxygenator thus providing for the elimination of the venous blood reservoir, and a lessened tubing circuit.

Other objects, features and advantages of the invention will become evident from the foregoing detailed description of the invention taken in conjunction with the drawings.

DESCRIPTION OF THE DRAWINGS

The structure, operation, and advantage of the invention will become further apparent upon consideration of the following description taken in conjunction with the accompanying drawings, wherein.

DETAILED DESCRIPTION OF THE INVENTION

The present invention is directed to an extracorporeal membrane oxygenator having a dual pump system where the first pump, in the current embodiment, is an axial flow pump whose primary function is to create secondary flows in the body of the oxygenator at low pressures thereby improving the membrane gas transfer efficiency.

The second pump, in the current embodiment, is a servo controlled centrifugal pump whose function is to return oxygenated blood back to the patient while maintaining low positive pressure at all times independent of flow rate and afterload pressure, while the oxygenator portion of the device consists of two readily made cylindrical membranes suspended in a housing forming a tubular flow channel, requiring blood to follow a complicated spiral path such that its effective contact time with the gas exchange membranes is prolonged.

Figure 1:
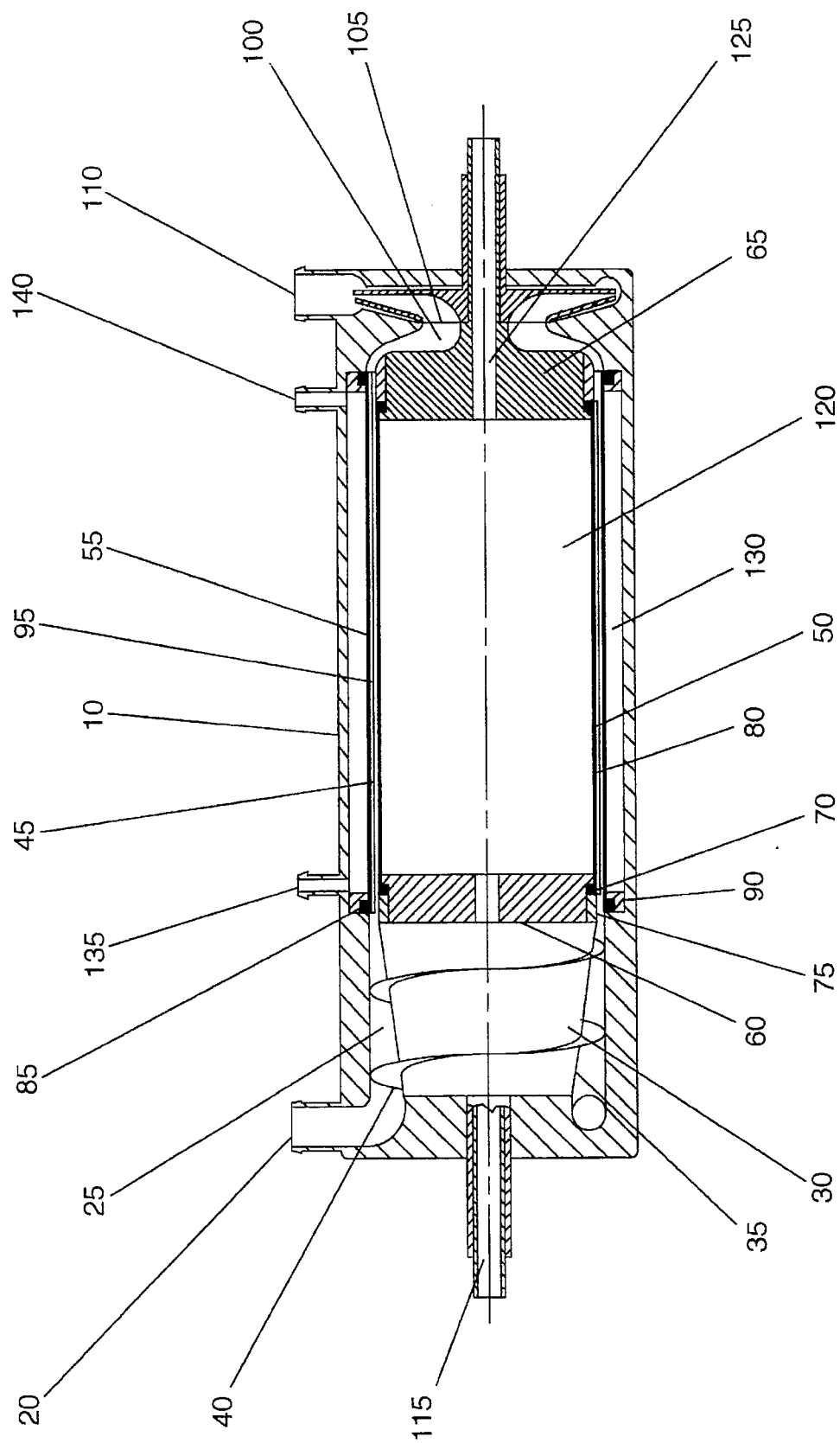
FIG. 1 is a cross-sectional view of the invention.

Referring now to FIG. 1, there is shown an extracorporeal membrane oxygenator comprised of housing 10, consisting of plastic such as polycarbonate. At inflow end of housing 10, is blood inflow port, 20. Blood inflow port 20 leads into axial flow pump chamber, 25. Axial flow pump chamber 25, houses axial flow pump rotor, 30, consisting of pump rotor hub, 35, and pump rotor vanes, 40, and leads into cylindrical blood flow channel 45. Cylindrical blood flow channel 45 is formed by two concentric membranes, inner membrane, 50, and outer membrane, 55. Inner membrane 50, is supported at inflow end by membrane inflow support bulkhead, 60, and at outflow end by membrane outflow support bulkhead, 65.

Adhered to each end of inner membrane are inner membrane seal, 70, which is let into grooves or retention features in membrane inflow support bulkhead, 60, and membrane outflow support bulkhead, 65. Securing inner membrane 50 to support bulkhead 65 are inner membrane retainer, 75. Surrounding and in close approximation to inner membrane 50 is inner membrane support, 80.

Outer membrane, 55, is secured to housing, 10, by means of outer membrane seal, 85, adhered to each end, and retained by outer membrane retainer, 90. Outer membrane, 55, is supported on inner surface by outer membrane support, 95. Outflow end of cylindrical blood flow channel 45 leads into centrifugal pump inlet, 100, which leads to centrifugal pump rotor, 105, then to blood outflow port, 110.

Located at or near inflow end of housing 10, is central gas inlet, 115. Central gas inlet, 115, leads through axial pump rotor,30, membrane inflow support bulkhead, 60, into central chamber, 120. Leading out from central chamber, 120, is gas outflow port, 125, which passes through membrane outflow support bulkhead, 65, centrifugal pump rotor, 105, and housing, 10.

Located between outer membrane. 55, and housing, 10, is outer cavity, 130. Passing through housing, 10 and leading to inflow end of outer cavity, 130, is outer cavity gas inlet port, 135. Leading from outflow end of outer cavity, 130, and through housing, 10, is outer cavity gas outlet port, 140.

Figure 2:
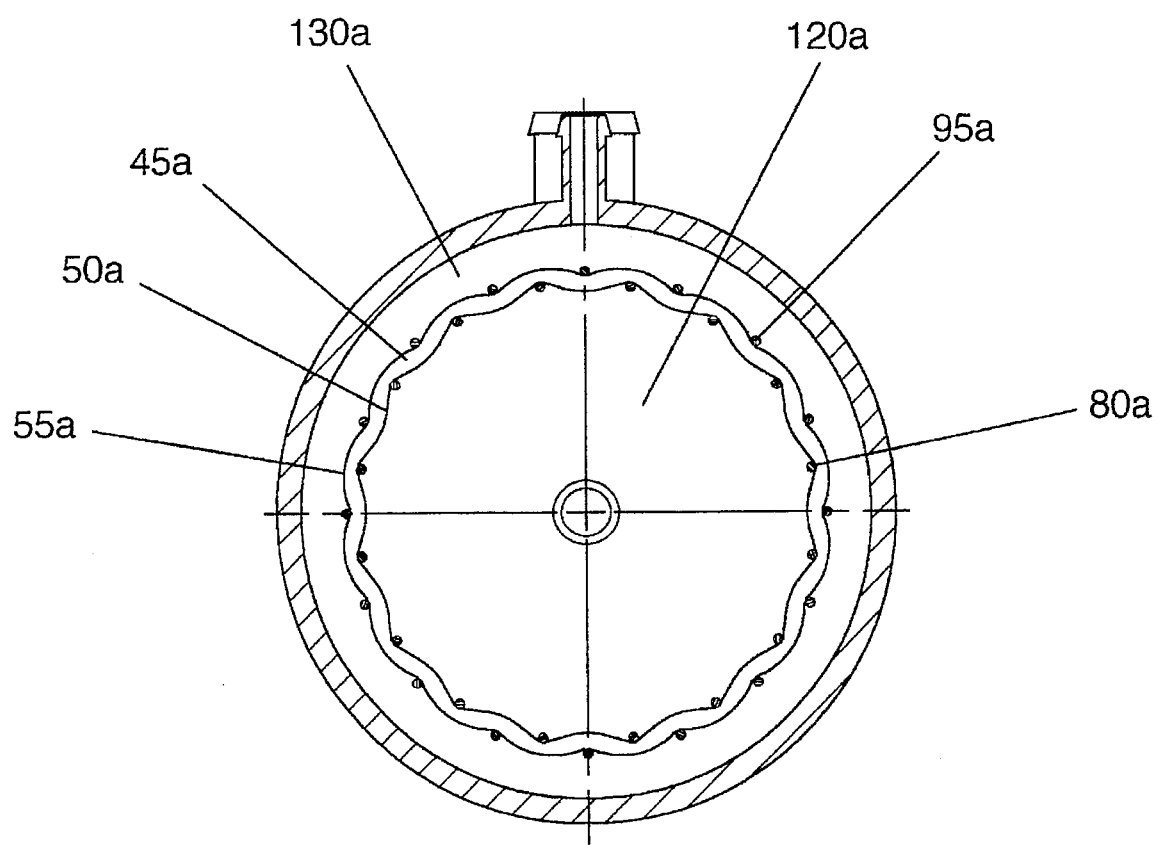
FIG. 2 is a cross sectional view showing the gas interchange interface using this invention.

Other and further embodiments of the present invention may be provided. Referring now to FIG. 2, another embodiment of the present invention is shown in which like parts to those in FIG. 1 are similarly numbered with the addition of the suffix "a".

Referring to FIG. 2, there is shown a transverse cross sectional view of an extracorporeal membrane oxygenator. Inner chamber, 120a, is separated from cylindrical blood flow channel 45a, by inner membrane support, 80a, and inner membrane, 50a. Intermediate blood flow channel, 45a, is separated from outer chamber, 130a, by outer membrane, 55a, and outer membrane support, 95a.

Referring again to FIG. 1, blood coming from the patient, flows into blood inflow port, 20, and into axial pump chamber, 25. Rotation of axial pump rotor, 30, causes pump rotor vanes, 40, to act upon blood producing a complex flow pattern in which blood is induced to flow through intermediate cylindrical blood flow channel 45, to centrifugal pump, 105, where it is caused to flow through blood outflow port, 110, and to the patient. Angular momentum is provided to the blood as it flows from axial pump chamber, 25, and into cylindrical blood flow channel 45 producing a spiral flow pattern containing complex secondary flows.

Referring again to FIG. 2, blood flowing within intermediate chamber. 45a, is at a greater pressure than pressure within central chamber, 120a, and outer chamber, 130a, producing a slight distortion of inner membrane, 50a, and outer membrane, 55a. The influence of inner membrane support, 80a, and outer membrane support, 95a, produces a pattern in the distortion of inner membrane, 50a, and outer membrane, 55a, which acts upon the flowing blood and induces turbulence, which enhances gas transfer by diffusion, and reduces risk of thrombus formation.

Figure 3:
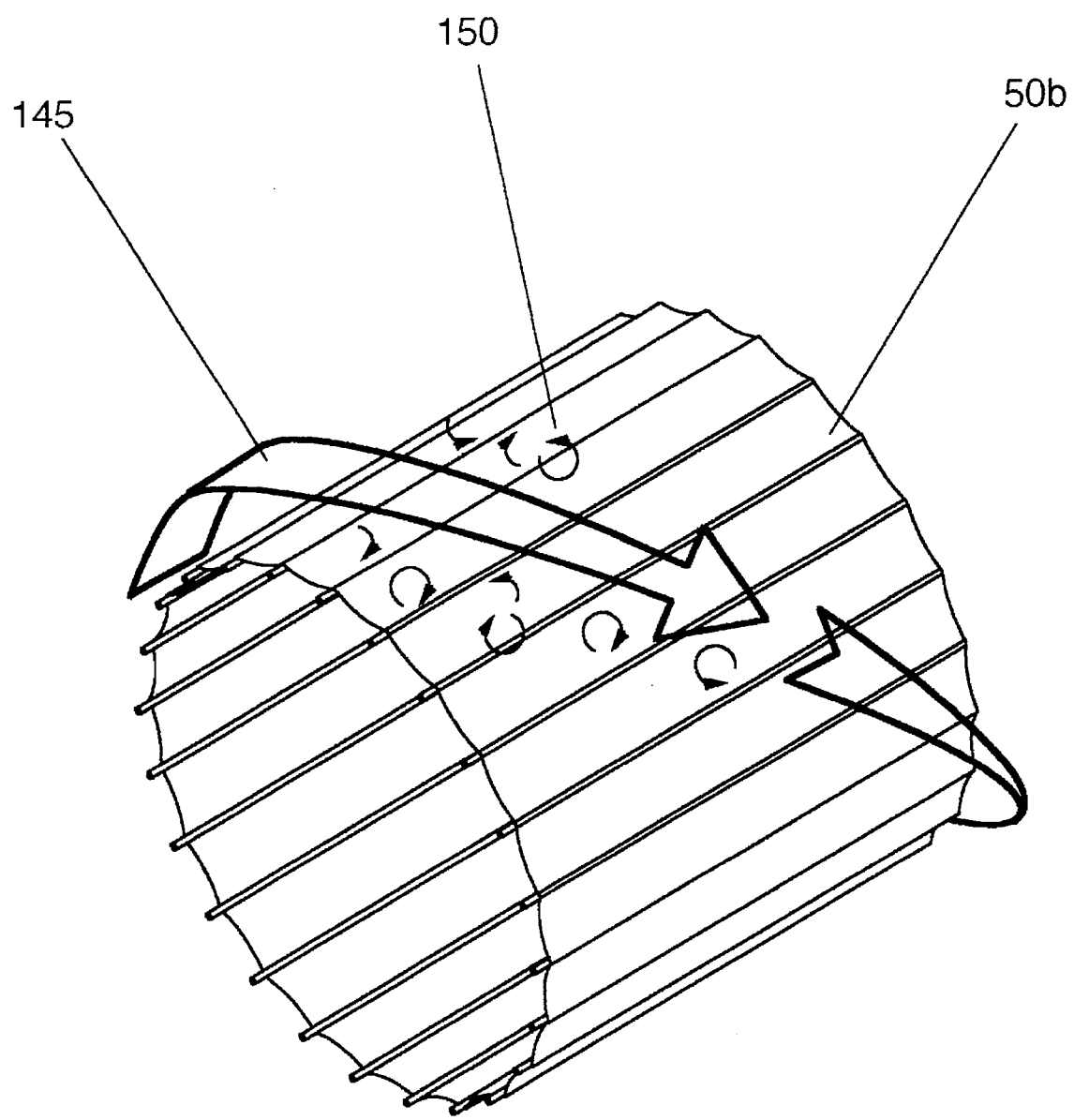
FIG. 3 is a representation of the helical primary and complex secondary blood flowpath across the surface of the inner membrane.

Referring now to FIG. 3, another embodiment of the present invention is shown in which like parts to those in FIG. 1 are similarly numbered with the addition of the suffix "b". In the interest of clarity, outer membrane, 55, and outer membrane support, 95, are not depicted. Blood flow paths are designated by arrows. Primary blood flow, 145, moves along a helical path. Secondary flows, 150, are induced by viscous interaction with surface of inner membrane, 50b, and distortions present on surface of inner membrane, 50b, which enhances gas transfer by diffusion, and reduces risk of thrombus formation. Flow characteristics depicted for interface between blood and surface of inner membrane, 50b, are similar to flow characteristic present at surface of outer membrane, 55.

Referring again to FIG. 1 gas flows through inner cavity, 120, and outer cavity, 130, along surface of inner membrane, 50, and outer membrane, 55. Differences in concentration of various gases in blood, and gas produce diffusion gradients across inner membrane, 50, and outer membrane, 55, inducing transfer of oxygen from gas into blood and carbon dioxide and other waste gases from blood into gas stream.

I claim:

1. An extracorporeal membrane oxygenator for the extracorporeal oxygenation of blood and removal of carbon dioxide from said blood in neonatal patients, where said extracorporeal membrane oxygenator is comprised of a polycarbonate housing with a plurality of projections located at each end of said polycarbonate housing, where said projections provide a means for the inflow and outflow of gases and blood, and located within said polycarbonate housing are:

1) an axial flow pump; comprising pump rotor vanes, and an axial pump rotor whereby an axial pump rotor means is provided to rotate said pump rotor vanes thereby inducing blood to flow in a spiral manner through a blood inflow port and into a blood inflow chamber, 2) a blood inflow port; where said axial flow pump is in communication with said blood inflow port, 3) a blood inflow chamber where said blood inflow port is in communication with said blood inflow chamber, 4) an inner gas exchange cavity, 5) an outer gas exchange cavity, 6) a cylindrical blood flow channel whereby said cylindrical blood flow channel is located between and surrounded in a cylindrical fashion by said inner gas exchange cavity and said outer gas exchange cavity, 7) a central gas inlet port; whereby a means is provided to introduce oxygen into said inner gas exchange cavity, 8) an outer gas inlet port, whereby a means is provided to introduce oxygen into said outer gas exchange cavity, 9) an inner concentric gas exchange membrane surrounding outside of said inner gas exchange cavity, whereby a means is provided to internally support said gas exchange membrane in a concentric manner, 10) an outer concentric gas exchange membrane surrounding outside of said outer gas exchange cavity, whereby a means is provided to externally support said gas exchange membrane in a concentric manner, 11) a central gas outlet port, where said central gas outlet port is in communication with said inner gas exchange cavity, 12) an outer gas outlet port, where said outer gas outlet port is in communication with said outer gas exchange cavity, 13) a centrifugal pump comprised of a centrifugal pump housing and a centrifugal pump rotor, whereby said centrifugal pump is in communication with said blood outflow port, whereby a means is provided to return oxygenated blood to a patient.

2. The extracorporeal membrane oxygenator of claim 1 wherein said outer and inner concentric gas exchange membranes are constructed of microporous polysulfone or a microporous polytetrafluoroethylene.

3. The extracorporeal membrane oxygenator of claim 2 whereby a means is provided wherein said centrifugal flow pump is controlled by a fixed Volume closed loop control system whereby the rotational rate of said centrifugal pump is adjusted in response to changes in afterload pressure of said extracorporeal membrane oxygenator.

4. The extracorporeal membrane oxygenator of claim, 3 whereby said inner concentric gas exchange membrane is supported internally by an internal membrane retainer.

5. The extracorporeal membrane oxygenator of claim 4 whereby said outer concentric gas exchange membrane is supported externally by an outer membrane retainer.

* * * * *